United States Patent [19]

Finney et al.

[11] 4,201,202
[45] May 6, 1980

[54] PENILE IMPLANT

[75] Inventors: Roy P. Finney, Tampa, Fla.; Henry W. Lynch, Racine, Wis.

[73] Assignee: Medical Engineering Corp., Racine, Wis.

[21] Appl. No.: 945,757

[22] Filed: Sep. 25, 1978

[51] Int. Cl.² .............................................. A61F 5/00
[52] U.S. Cl. ............................................ 128/79; 3/1
[58] Field of Search .................. 128/79, DIG. 20; 3/1

[56] References Cited

U.S. PATENT DOCUMENTS

| | | | |
|---|---|---|---|
| 3,752,150 | 8/1973 | Harris | 128/25 |
| 3,853,122 | 12/1974 | Strauch et al. | 128/79 |
| 3,954,102 | 5/1976 | Buuck | 128/79 |
| 4,009,711 | 3/1977 | Uson | 128/79 |
| 4,066,073 | 1/1978 | Finney et al. | 128/79 |

Primary Examiner—Lawrence W. Trapp

[57] ABSTRACT

A penile prosthesis which is adapted to be surgically implanted in man for the treatment of erectile impotence includes two separate penile implants each comprising an elongated, flexible rod having a short proximal portion of relatively stiff material which is adapted to be implanted into the root end of the corpus cavernosum to support the implant and a longer distal portion of softer material which is adapted to be implanted into the corpus cavernosum of the pendulus penis. A flexible, cylindrical sleeve is positioned axially about an intermediate section of the distal portion of the rod and is sealed at its ends to the rod in a fluid tight manner to form a chamber for pressurizing fluid. The implant also includes a pressure bulb for pressurizing fluid; tubing communicating between the chamber and the pressure bulb; and valve means for controlling the flow of fluid between the pressure bulb and the chamber. In a preferred embodiment, the entire implant is made of silicone elastomer and the pressure bulb is sized to be implanted into the scrotal sac.

8 Claims, 5 Drawing Figures

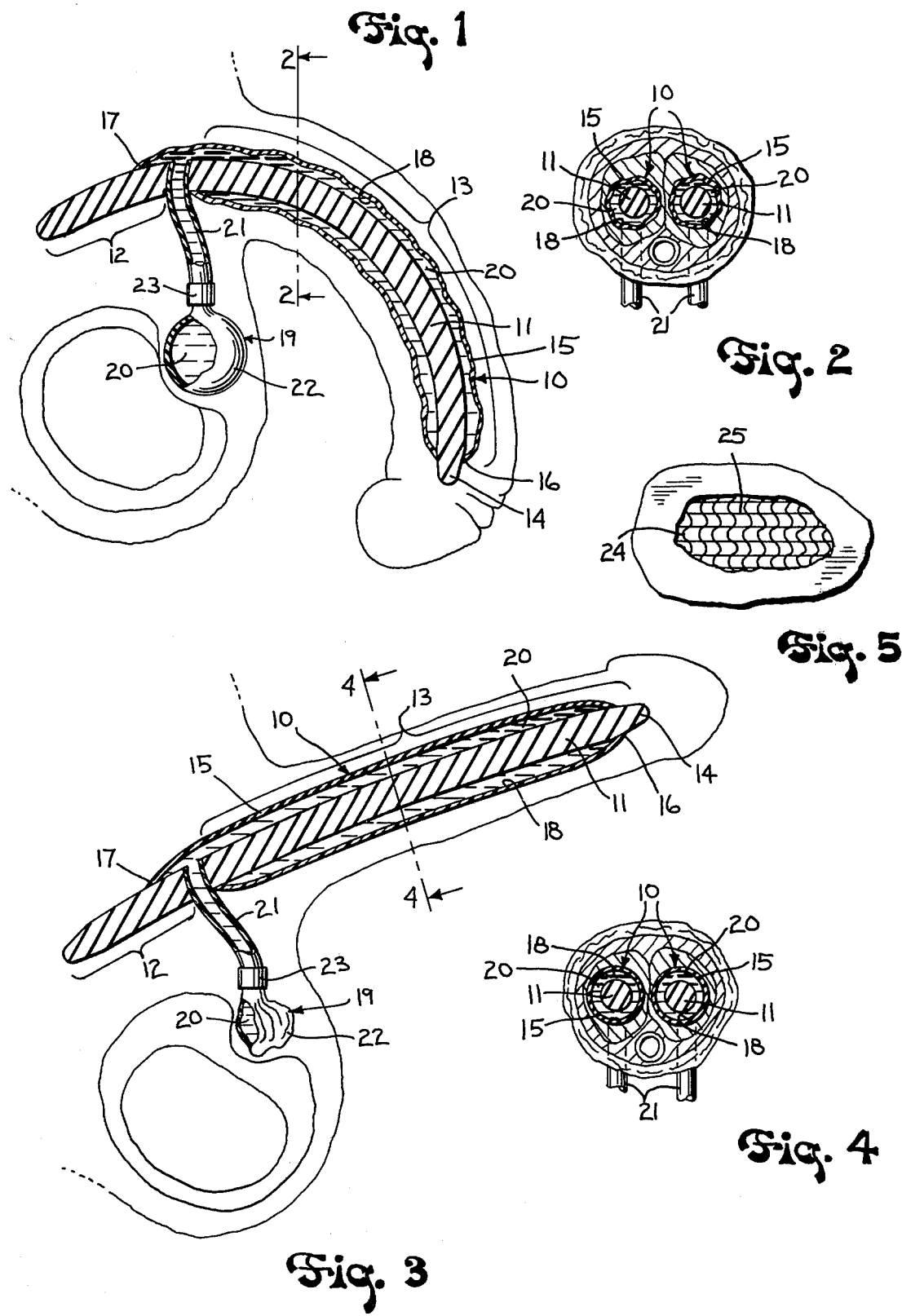

PENILE IMPLANT

BACKGROUND OF THE INVENTION

In some instances of erectile impotence in which the patient does not respond to more conventional therapy, the surgical implanting of a penile prosthesis may be the only practical means of remedying the impotency.

In the past, several types of penile prostheses have been employed. The first type is a rod of suitable stiffness which is surgically implanted into the corpus cavernosum of the penis. The major disadvantage of the rod-type implant is the permanent stiffness of the rod which can be a source of physical pain as well as embarrassment to the patient. The rod-type prostheses disclosed in U.S. Pat. Nos. 3,853,122 and 4,066,073 are attempts to overcome that disadvantage.

The other type of penile prosthesis which is available is the inflatable prosthesis. The most common inflatable prosthesis includes two fairly long inflatable tubes that are surgically implanted in the corpus cavernosum of the penis. Each of the two tubes is connected by tubing to a pressure bulb of inflating fluid which is implanted elsewhere in the body. Because of the volume required to pressurize and rigidize the inflatable tubes, the pressure bulbs are relatively large. In the prosthesis of U.S. Pat. No. 3,954,102 the fluid is supplied from a single relatively large reservoir which is implanted in the abdominal cavity.

The inflatable penile prosthesis of U.S. Pat. No. 4,009,711 includes two implants each having its own relatively large pressurizing bulb which is surgically implanted in the scrotal sac. The penile implant includes a non-distensible stem portion made of a relatively stiff silastic material which supports the implant and an integral collapsible bag-like distensible portion which is implanted into the cavernosum of the pendulus penis.

Inflatable implants currently available must be inflated periodically to prevent the scar tissue capsule which forms about the implant from bridging folds in the fabric of the inflatable or distensible portion and preventing the implant from becoming fully inflated.

SUMMARY OF THE INVENTION

It is the general object of the present invention to disclose a superior inflatable penile prosthesis.

The present invention contemplates a penile implant including an elongated, flexible rod having a short, proximal portion of relatively stiff material which is adapted to be implanted into the root end of the corpus cavernosum to support the implant and a longer distal portion of softer and more flexible material adapted to be implanted in the corpus cavernosum of the pendulus penis. A flexible, distensible, cylindrical sleeve is positioned axially about an intermediate section of the distal portion of said rod and the ends of the sleeve are sealed to the rod in a fluid tight manner to form a chamber for receiving pressurizing fluid. The implant also includes a pressure bulb for pressurizing fluid, tubing communicating between the chamber and the pressure bulb, and valve means for controlling the flow of the pressurizing fluid between the pressure bulb and the chamber. In a preferred form of the invention, there are two separate penile implants each having its own separate pressure bulb which is adapted to be implanted into the scrotal sac.

The relatively stiff, proximal portion of the flexible rod of the implant of the present invention is adapted to be implanted into the root end of the corpus cavernosum to anchor and support the implant and the longer, relatively soft and more flexible distal portion of the rod is adapted to be implanted into the corpus cavernosum of the pendulus penis. The more flexible, soft distal portion of the rod causes a minimum of irritation to the tissue of the penis and permits the pendulus penis to assume a normal position when the implant is not inflated. In a preferred embodiment, the tip of the distal portion of the rod is parboloidal in shape to fit the end of the corpus cavernosum, and to enhance the physiological compatibility of the implant.

The relatively small volume chamber which is formed by sealing the ends of the axially positioned cylindrical sleeve to and about the rod normally contains residual pressurizing fluid and it can be further pressurized with a small amount of fluid from the pressure bulb to rigidize the implant and to affect a penile erection. The presence of the rod in the chamber also effectively prevents the transfer of too much fluid back to the pressure bulb. The portion of the flexible rod which extends through the pressurizing chamber also prevents the fabric of the sleeve which forms the outer wall of the chamber from forming deep folds when the implant is deflated. The scar tissue of the capsule which surrounds the implant otherwise could bridge such folds preventing the implant from becoming fully inflated when later pressurized.

BRIEF DESCRIPTION OF THE DRAWINGS

FIG. 1 is a partial sectional view of the penile prosthesis of the present invention in a depressurized condition as surgically implanted in a male;

FIG. 2 is a cross sectional view taken along the lines 2—2 of FIG. 1;

FIG. 3 is a view similar to FIG. 1, except the prosthesis is fully pressurized;

FIG. 4 is a view taken along line 4—4 in FIG. 3; and

FIG. 5 is an enlarged view of a preferred sleeve fabric.

DESCRIPTION OF THE PREFERRED EMBODIMENT

As seen in FIGS. 1–4, the penile implant 10 comprises an elongated rod 11 of a physiologically inert material such as medical application silicone rubber. The rod 11 has a short, proximal portion 12 of relatively stiff material which is implanted in the root end of the corpus cavernosum to support and anchor the implant, and a longer distal portion 13 of a softer, more flexible material which is implanted into the corpus cavernosum of the pendulus penis. The distal portion 13 has a tip 14 which is paraboloidal in shape to conform to the inner shape of the end of the corpus cavernosum.

Positioned axially about an intermediate section of the distal portion 13 is a sleeve 15 of silicone coated fabric which is sealed at its ends 16 and 17 to the rod in a fluid-tight manner to form a cylindrical chamber 18 for pressurizing fluid. The seals between the ends 16 and 17 of the sleeve 15 and the rod 11 are preferably made with a suitable silicone adhesive.

Referring to FIGS. 1 and 3, it can be seen that communication between the chamber 18 and a pressure bulb assembly 19 containing a pressurizing fluid 20, such as saline is provided by a length of silicone rubber tubing 21. The pressure bulb assembly 19 which is implanted in the scrotal sac includes a pressure bulb 22 and a valve 23 for controlling the flow of pressurizing fluid 20 between the pressure bulb 22 and the chamber 18. The valve means 23 is preferably a normally closed valve which is opened manually by squeezing the valve body or the pressure bulb and which can either be closed by additional manipulation or which although not completely closed delays the return of fluid to the bulb for a suitable period of time. Suitable valves are disclosed in U.S. Pat. Nos. 4,009,711 and 4,060,080.

Referring specifically now to FIG. 1, it can be seen that when the chamber 18 of the implant is depressurized the soft, relatively flexible distal portion 13 of the rod 11 permits the penis to assume a substantially normal, flaccid position. As seen only in FIG. 2, the chamber 18 contains a small amount of residual fluid 20 even when the implant 10 is depressurized. The residual fluid 20 within the chamber 18 cooperates with the rod 11 to keep the fabric of the sleeve 15 from forming deep folds into which the scar tissue of the capsule which forms about the implant 10 can grow to interfere with the later expansion of the chamber.

Referring now to FIGS. 3 and 4, it can be seen that when the penile implant 10 is pressurized the chamber 18 is filled and distended by pressurized fluid 20 and the soft, flexible distal portion 13 of the rod 11 is supported by the pressurized sleeve 15 so that the penis assume a substantially normal erectile form.

As seen in the drawings in both its depressurized and pressurized states the proximal portion 12 of the penile implant 10 is anchored in the root end of the corpus cavernosum, and the paraboloidal tip 14 is positioned in the glans end of the corpus cavernosum. As a result, the implant 10 is at all times positioned correctly in the corpus cavernosum of the penis and the likelihood of displacement is minimized.

Although in the drawings a single penile implant 10 is shown, the complete penile prosthesis will normally include two separate penile implants each having its own pressurizing bulb which is surgically implanted in the scrotal sac.

The unique construction of the penile implant of the present invention which includes an intermediate section of the distal portion of the rod 11 within the chamber 18 minimizes the amount of fluid 20 needed to pressurize and rigidize the implant 10. As a result, the pressure bulbs 22 can be relatively small in size, approximately 10 to 15 cc in volume, and thus, can be conveniently implanted in the scrotal sac, if desired, replacing the testes.

The pressure bulb 22 which is of flexible resilient material can be provided with a small, integral resealable valve (not shown), if desired, so that additional fluid can be added to the pressure bulb 22 with a hypodermic needle after the bulb 22 has been implanted. A suitable resealable valve is disclosed in U.S. Pat. No. 3,919,724.

To effect a penile erection, the chamber 18 of a properly implanted prosthesis is filled by forcing pressurizing fluid 20 from the pressure bulb 22 through the valve 23 via the tubing 21 into the chamber 18 formed by the rod 11 and sleeve 15. The pressurizing fluid 20 fills the chamber 18 and stiffens the penis adequately for sexual intercourse. When it is desired to depressurize the implant 10, the pressurizing fluid 20 is permitted to drain from the chamber 19 back via the tubing 21 through the valve 23 into the pressure bulb 22. Once an adequate amount of fluid 20 has been returned to storage in the pressure bulb 22 the penis is flaccid and the patient can engage in activities without fear of embarrassment or pain.

In the foregoing description, the proximal portion 12 of the rod 11 has been described as being stiff whereas the distal portion 13 has been described as being relatively flexible. While the term "stiff" has been used to descirbe the desired physical properties of the material of the rod, a more precise and technical term is flexural modulus, which is the ratio of applied force to resulting deflection. However, most tables of properties do not describe the stiffness properties of rubber or rubber-like material. However, they do list related properties such as hardness.

Hardness is measured by a durometer such as a Shore A durometer which ascertains the depth of penetration of a specific indentor into a specimen under specified conditions. A scale is chosen so that 9 represents a material showing no measurable resistance to indentation and 100 represents a material showing no measurable indentation.

In the preferred embodiment of the invention, the proximal portion 12 of the rod 11 has a Shore hardness of about 70, the distal portion 13 has a Shore hardness of about 20, and the material has sufficient tensile strength for its intended use. Although a material of the described characteristics is preferred, any material which performs satisfactory under conditions of use can be employed.

The rod 11 is preferably molded as a single piece or the distal and the proximal portions can be joined by a hinge of the type disclosed in U.S. Pat. No. 4,066,073. The stiffness of a silicone rod can be controlled by the type and amount of catalyst used to cure the elastomer and the amount of heat and time employed during the curing or vulcanizing process.

The rod 11 may take other form than that described. For example, the rod may instead of being a solid silicone piece be a cylinder of sponge or foam, with or without reinforcement. Therefore, the word "rod" as used in the specification and claims is intended to cover any structure functionally equivalent to that described for purposes of illustration.

The sleeve 15 is preferably made of a silicone elastomer coated woven or knit fabric which provides to a limited predetermined expansion to allow the penis to become longer and to contain the pressure so that the tunica albuginea will not distend. A preferred form of woven fabric is shown in FIG. 5. As seen in the drawing, the axial threads 24 of the fabric are normally crimped and the longitudinally extending threads 25 are straight. A silicone coated fabric of this design will expand to a limited extent axially and not expand longitudinally. Alternatively, the sleeve 15 also can be made of a material which does not distend either axially or longitudinally.

The diameter of the sleeve 15 is preferably such that the rod 11 fills the major portion of the chamber 18. Therefore, even when the implant is depressurized and the sleeve is of the nonexpanding fabric, the rod 11 will cooperate with the small amount of residual fluid 20 which remains in the chamber 18 to prevent deep folds from forming in the fabric of the sleeve. The use of a sleeve material which does not distend or distends only to a limited extent makes it possible to raise the fluid pressure in the sleeve to the desired high level with only a minimum of pressurizing fluid. Therefore, small volume pressure bulbs which can be implanted in the scrotal sac can be used.

The preferred method of implantation of implant 10 is through the perineum. After appropriate incision, the corpus cavernosum is dilated distally and proximally to accept the implant. The appropriate anatomical measurements are made to insure that the proximal portion 12 of implant 10 will be positioned at the base of the penis below the pelvic bone. An implant having an appropriately sized distal portion 13 is obtained and the distal portion inserted into the corpus cavernosum of the penis. The proximal portion 12 of implant 10 is cut to the appropriate length. During the manufacture of implant 10 the length of proximal portion 12 may be deliberately made longer than necessary thereby permitting it to be trimmed to the correct length at the time of surgery. Only one implant of each distal portion length need, therefore, be available since other anatomical size variations may be accommodated by trimming proximal portion 12. This greatly reduces the number of implant sizes which must be produced over that which would be required if no such size alteration were possible.

Proximal portion 12 is inserted in the dilated crus after trimming. The incision is then closed. The identical procedure is preformed on the other side of the penis to complete the surgical procedure. Distal portions 12 of the two implants may diverge laterally to accommodate the anatomy and provide lateral stability to the penis.

In the preferred embodiment, all the parts and components of the prosthesis are made of medical application silicone rubber which is non-reactive, non-toxic and well tolerated by the adjacent organic tissues. Silicone rubber is preferred because it is quite resistant to wear and tear and remains functional for long periods of time. However, other suitable materials may be employed, if desired.

It will be readily apparent to those skilled in the art to which this invention relates that a variety of changes and modifications might be made without departing from the spirit and scope of the invention.

For example, although in the drawings the tubing 21 is shown as passing through the rod 11 and emptying directly into the chamber 18 other constructions may be employed. For instance, the intermediate portion of the rod 11 within the chamber 18 could be provided with a central bore and wall openings that communicate with the bore and chamber so that the tubing 21 could communicate directly with the bore and indirectly with the chamber. Another modification that could be made would be to have the tubing 21 not pass through the body of the rod 11, but communicate with the chamber 18 through a port in the wall of the sleeve 15.

Further more, if desired, the sleeve 15 may take the initial shape of a curved tubular member as opposed to the cylinder described and shown in the drawings. The forming of a curved tubular sleeve in approximately the shape that the sleeve assumes when the implant is in the depressurized state further minimizes the likelihood of folds forming which can be encapsulated by scar tissue. However, in order to permit the curved tubular sleeve to assume the shape of a cylinder upon pressurization, it may be necessary to have selected longitudinal threads of the woven or knit fabric of the sleeve crimped to permit a limited longitudinal extension.

From the foregoing, it will be apparent that the description has been for purposes of illustration and is not intended to be limiting.

What is claimed is:

1. A penile implant comprising:
   (a) an elongated, flexible rod of physiologically inert material having a relatively short proximal portion adapted to be inserted into the root end of the corpus cavernosum of a penis, and a longer distal portion adapted to be implanted in the corpus cavernosum of the pendulous penis;
   (b) a sleeve axially positioned about an intermediate section of the distal portion of said rod and sealed at each end of the rod to form an elongated pressurizable chamber;
   (c) a pressure bulb for pressurizing fluid for said chamber;
   (d) means connecting the chamber and the pressure bulb so that pressurizing fluid can be introduced into and removed from the chamber; and
   (e) valve means for controlling the flow of fluid between the chamber and the bulb.

2. The implant of claim 1 in which the distal portion has a tip of paraboloidal shape to conform to the normal shape of the tip of the corpus cavernosum.

3. The implant of claim 1 in which the proximal portion of the rod has a stiffness of about 70 Shore.

4. The implant of claim 1 in which the distal portion of the rod has a stiffness of about 20 Shore.

5. The implant of claim 1 in which the components are made of silicone rubber.

6. The implant of claim 1 in which the sleeve is comprised of a fabric coated with silicone rubber which fabric expands to a predetermined limited extent to allow the penis to become larger and to contain the pressure so that the tunica albuginea will not distend.

7. The implant of claim 6 in which the sleeve is formed of a silicone coated fabric which has axial threads that are crimped when the chamber is not pressurized and the degree of axial expansion of the sleeve is limited to that afforded by the straightening of the axial threads.

8. The method of implanting the implant of claim 1 in the penis of a human male which comprises incising the penis to expose the corpus cavernosum, positioning the proximal portion at the base of the penis below the pelvic bone and positioning the paraboloidal tip of the distal portion in the glans end of the corpus cavernosum so that the likelihood of displacement of the implant is minimized.

* * * * *